(12) United States Patent
Wieters

(10) Patent No.: US 11,925,325 B2
(45) Date of Patent: Mar. 12, 2024

(54) MEDICAL SYSTEM, MEDIA AND/OR ENERGY SOURCE, AND TROCAR

(71) Applicant: Olympus Winter & Ibe GmbH, Hamburg (DE)

(72) Inventor: Martin Wieters, Barsbuettel (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 106 days.

(21) Appl. No.: 17/179,656

(22) Filed: Feb. 19, 2021

(65) Prior Publication Data

US 2021/0259530 A1    Aug. 26, 2021

(30) Foreign Application Priority Data

Feb. 21, 2020    (DE) .......................... 102020104574.3

(51) Int. Cl.
*A61B 1/018*    (2006.01)
*A61B 1/00*    (2006.01)
(Continued)

(52) U.S. Cl.
CPC .......... *A61B 1/018* (2013.01); *A61B 1/00016* (2013.01); *A61B 1/063* (2013.01);
(Continued)

(58) Field of Classification Search
CPC . A61B 1/018; A61B 17/34; A61B 2560/0462; A61B 2090/0807;
(Continued)

(56) References Cited

U.S. PATENT DOCUMENTS 5,961,514 A * 10/1999 Long ..................... A61B 17/34
606/41
2005/0077689 A1* 4/2005 Hueil ................. A61B 17/3462
277/628
(Continued)

FOREIGN PATENT DOCUMENTS

DE    20 2007015 093 U1    2/2008
DE    10 2011 088 336 A1    6/2013
(Continued)

OTHER PUBLICATIONS

1 German Office Action dated Feb. 21, 2020 issued in DE 10 2020 104 574.3.
(Continued)

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

A medical system including: a trocar configured to provide an artificial access to a body cavity of a patient; a medical instrument configured to be inserted through the trocar and into the body cavity of the patient for performing a medical function in the body cavity of the patient; and a controller configured to: determine whether the medical instrument is inserted into the trocar; and enable the performing of the medical function by the medical instrument only if the medical instrument is determined to be inserted into the trocar.

13 Claims, 3 Drawing Sheets

(51) Int. Cl.
  *A61B 1/06*  (2006.01)
  *A61B 1/12*  (2006.01)
  *A61B 17/34* (2006.01)
(52) U.S. Cl.
  CPC .............. *A61B 1/125* (2013.01); *A61B 17/34* (2013.01); *A61B 2560/0462* (2013.01)
(58) Field of Classification Search
  CPC ........ A61B 1/00124; A61B 2090/0805; A61B 1/0125; A61B 2017/3419; A61B 1/00154; A61B 1/00142; A61B 1/00135; A61M 2039/0626; A61M 39/06
  See application file for complete search history.

(56) References Cited

U.S. PATENT DOCUMENTS

| | | | | |
|---|---|---|---|---|
| 2008/0249467 A1* | 10/2008 | Burnett | .................. | A61B 1/313 604/117 |
| 2009/0281478 A1* | 11/2009 | Duke | .................... | A61B 17/34 604/22 |
| 2010/0106157 A1* | 4/2010 | Umemoto | .......... | A61B 18/1492 606/41 |
| 2010/0204698 A1* | 8/2010 | Chapman | ........... | A61B 18/1442 606/51 |
| 2011/0098528 A1* | 4/2011 | Lewinsky | ............ | G02B 6/3624 600/104 |
| 2013/0053643 A1* | 2/2013 | Yoshida | ................. | A61B 1/126 600/114 |
| 2014/0121658 A1* | 5/2014 | Cosman, Jr. | ....... | A61B 18/1477 606/33 |
| 2014/0303437 A1* | 10/2014 | Kikuchi | ............. | A61B 1/00133 600/106 |
| 2015/0164547 A1 | 6/2015 | Sauter et al. | | |
| 2016/0175057 A1* | 6/2016 | Ibach | ................. | A61B 1/00066 600/103 |
| 2016/0192919 A1* | 7/2016 | Horii | ................ | A61B 17/00234 600/104 |
| 2016/0353969 A1* | 12/2016 | Kikuchi | .................. | A61B 34/20 |
| 2017/0086906 A1* | 3/2017 | Tsuruta | ................. | H02J 7/0042 |
| 2019/0201023 A1* | 7/2019 | Shelton, IV | ........... | G16H 30/20 |
| 2019/0201025 A1* | 7/2019 | Shelton, IV | ........... | A61B 5/065 |
| 2019/0201030 A1* | 7/2019 | Shelton, IV | ........... | A61B 34/30 |
| 2021/0022792 A1* | 1/2021 | Beaupre | ............. | A61B 17/3421 |
| 2021/0161437 A1* | 6/2021 | Thomas | .................... | G06F 9/06 |
| 2021/0259530 A1* | 8/2021 | Wieters | .................... | A61B 1/07 |
| 2021/0295980 A1* | 9/2021 | Ichikawa | ............ | G16H 40/63 |

FOREIGN PATENT DOCUMENTS

| | | | |
|---|---|---|---|
| DE | 10 2012 213 205 A1 | 5/2014 | |
| DE | 102016124730 A1 | 6/2018 | |
| EP | 1 520 539 A1 | 4/2005 | |
| EP | 3 626 200 a1 | 3/2020 | |
| ES | 2339768 T3 | 5/2010 | |
| JP | 09011887 A * | 1/1997 | |
| JP | 2013-48821 A | 3/2013 | |
| JP | 2014068987 A * | 4/2014 | ........ A61B 1/00016 |
| JP | 2016-7275 A | 1/2016 | |
| JP | 6469295 B1 | 2/2019 | |
| WO | 2018/232360 A1 | 12/2018 | |

OTHER PUBLICATIONS

European Search Report and Written Opinion dated Jun. 3, 2021 received in EP 21 15 4630.
Japanese Office Action dated Dec. 21, 2021 received in 2021-025714.
1 European Office Action dated May 3, 2023 received in 21 154 630.4.

* cited by examiner

MEDICAL SYSTEM, MEDIA AND/OR ENERGY SOURCE, AND TROCAR

CROSS-REFERENCE TO RELATED APPLICATION

The present application is based upon and claims the benefit of priority from DE 10 2020 104 574.3 filed on Feb. 21, 2020, the entire contents of which is incorporated herein by reference.

BACKGROUND

Field

The present disclosure relates to a medical system comprising a medical instrument and a trocar, wherein the trocar is configured to provide an artificial access to a body cavity of a patient, and the medical instrument is configured to be inserted through the trocar into the body cavity of the patient and for performing a medical function in the body cavity of the patient.

Furthermore, the present disclosure refers to a media and/or energy source and a trocar of a medical system.

Prior Art

Medical systems of the type mentioned above are used in modern medicine to perform operative procedures in body cavities of a patient without opening them extensively. Corresponding procedures are therefore also referred to as minimally invasive procedures.

In minimally invasive procedures, the procedure is usually controlled by means of an endoscope, which is inserted into the body cavity through a trocar, and which captures a video image of the body cavity. The video image is displayed on a monitor so that an attending physician can orient himself in the surgical field.

In order to capture an image of a body cavity with an endoscope, it is necessary to illuminate the endoscope's field of view. For this purpose, endoscopes usually comprise an illumination system consisting of optical fibers that run from a proximal end to a distal end of the endoscope. Illumination light may be fed in at the proximal end of the endoscope so that it is emitted at the distal end of the endoscope and illuminates the field of view of the endoscope.

The illumination light is usually generated by an external light source, which is connected to the endoscope via an optical fiber cable. LEDs or laser diodes are increasingly used as the light source. Laser diodes are mainly used as sources of excitation light for fluorescence examinations, but are also occasionally used to generate white illumination light.

When using laser diodes, however, it must be considered that the laser radiation they emit may be of such high intensity that it may cause injury if it hits an unprotected eye directly. While this is not a problem as long as the endoscope is inserted into the body cavity through the trocar, accidents may occur if the endoscope is not yet, or no longer, inserted into the body cavity at the beginning or end of a procedure, but is held freely in the hand by a physician. Accidents may also occur if the endoscope is briefly removed from the body cavity during a procedure, for example, for cleaning the optics.

Some endoscopes have a flushing device for the optics. A flushing medium, for example water, may be introduced into this flushing device from an external source, which is then delivered in the direction of the optics in order to clean them. However, if the external media source is activated when the endoscope is not currently inserted into the trocar, uncontrolled discharge of the medium may occur in the operating room. On the one hand, this leads to unnecessary contamination, and on the other hand, it may pose a further risk for accidents, e.g., due to slipping.

SUMMARY

It is therefore an object to provide a medical system which is improved with respect to the problems described.

Such object can be achieved by a medical system comprising a medical instrument and a trocar, wherein the trocar is intended for providing an artificial access to a body cavity of a patient, and the medical instrument is intended for being inserted through the trocar into the body cavity of the patient and for performing a medical function in the body cavity of the patient, wherein the medical system comprises a controller configured to determine whether the medical instrument is inserted into the trocar and to enable the performing of a medical function by the medical instrument only if the medical instrument is inserted into the trocar.

The configuration of the medical system ensures that the medical function is performed only when the medical instrument is inserted into the trocar. An unwanted negative effect of the medical function outside the body cavity under treatment or examination may thus be avoided.

According to an embodiment, the medical system may further comprise a media and/or energy source intended for providing media and/or energy for the execution of the medical function, and the controller may be configured to enable the provision of media and/or energy only when the medical instrument is inserted into the trocar. Such configuration may prevent the unintended dispensing of energy or media outside of the body cavity under treatment or examination.

In another embodiment of a medical system, the medical instrument may be an endoscope.

The media source may be intended for providing flushing fluid. In doing so, the delivery of flushing fluid outside the body cavity under examination or treatment and related problems and risks are avoided.

The energy source may comprise a light source, such as a laser light source. Light, especially laser light, may easily cause accidents and injuries if unintentionally emitted outside a body cavity under examination or treatment. Here, the disclosed embodiments may significantly increase the operational safety of a medical system.

In another embodiment of a medical system, the endoscope may have a shaft with a conductive surface, and the trocar may have at least one electrical contact which may be in contact with the shaft of the endoscope when it is inserted into the trocar.

The trocar may have two electrical contacts which are interconnected by the shaft of the endoscope when the endoscope is inserted into the trocar. By such configuration, the insertion of the endoscope into the trocar can be determined in a particularly uncomplicated manner.

In another embodiment of a medical system, the at least one electrical contact may be part of a seal of the trocar. The at least one electrical contact may be formed by a sealing element made of an electrically conductive elastic polymer. In such embodiment, the mechanical effort is particularly low.

In another embodiment of a medical system, the endoscope may comprise a shaft made of a magnetic material, and the trocar may comprise at least one coil whose inductance is altered when the endoscope is inserted into the trocar. In such configuration, insertion of the endoscope into the trocar may be detected without contact.

In another embodiment of a medical system, the trocar may comprise a capacitor whose capacitance is changed when the endoscope is inserted into the trocar. In such configuration, insertion of the endoscope into the trocar may also be detected without contact.

In another embodiment of a medical system, the trocar may comprise a tactile switch which is actuated when the endoscope is inserted into the trocar. In this way, insertion of the endoscope into the trocar can also be detected easily.

The controller of a medical system may comprise a circuit integrated in the trocar which determines whether the medical instrument is inserted into the trocar. The controller may be configured to provide a wireless or wired enabling signal when the medical instrument is inserted into the trocar. By integrating the circuit into the trocar, medical system can be implemented without the need for a separate device.

According to another embodiment, such object can be achieved by a media and/or energy source of a medical system according to the above embodiments, wherein the media and/or energy source is configured to receive the enabling signal of the controller, and to provide a medium or energy only when the enabling signal is present.

According to still another embodiment, such object can be achieved by a trocar of a corresponding medical system.

With respect to the advantages and effects achievable hereby, reference is expressly made to the above explanations.

BRIEF DESCRIPTION OF THE DRAWINGS

The embodiments will be explained in more detail below with reference to some exemplary drawings. In this context, the illustrated examples of embodiments are merely intended to contribute to a better understanding of the invention without limiting it.

The figures show.

DETAILED DESCRIPTION

Figure 1:
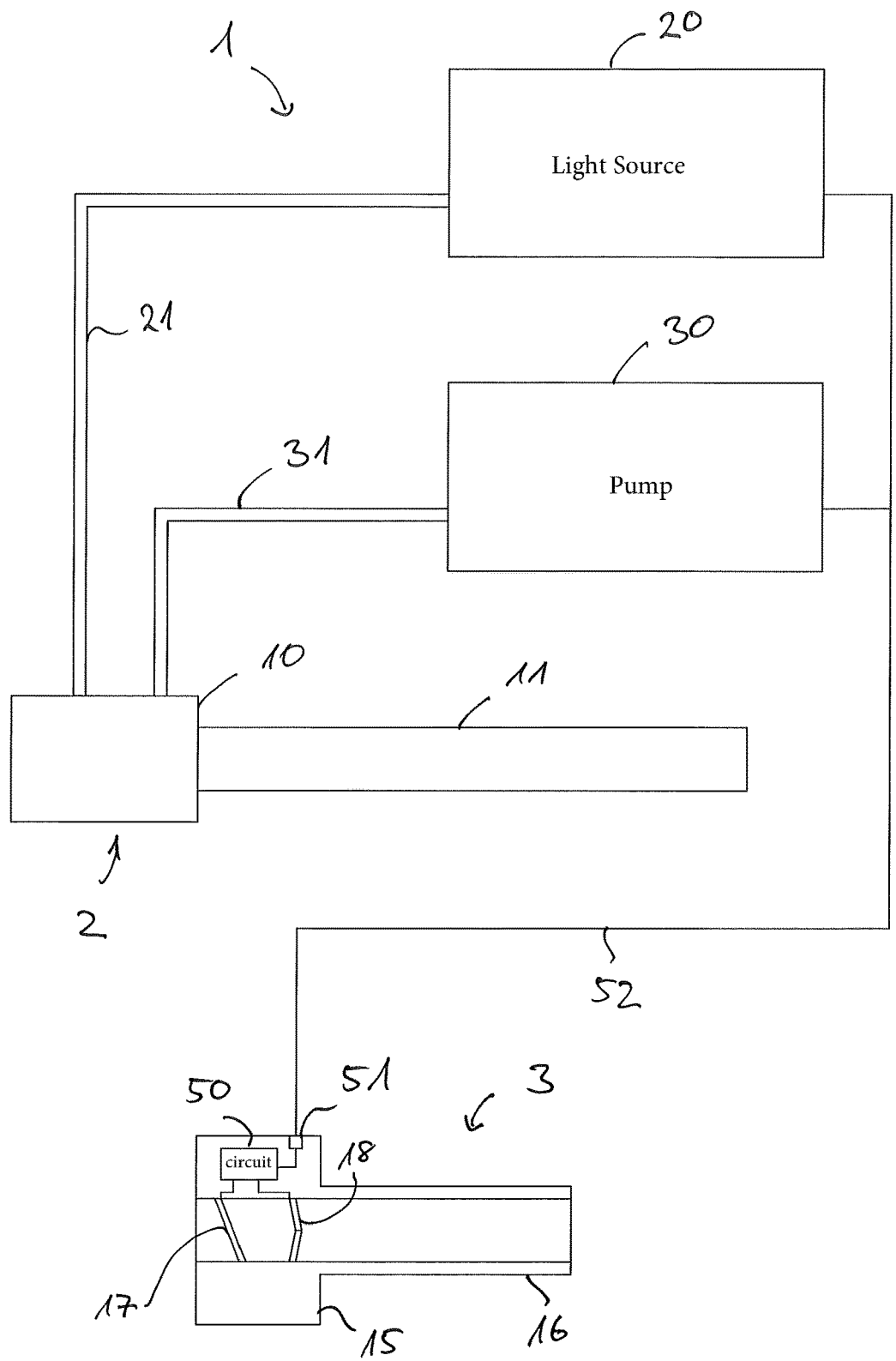
FIG. 1 illustrates a medical system.

FIG. 1 shows a medical system 1. The medical system 1 comprises a medical instrument in the form of an endoscope 2, and a trocar 3.

The endoscope 2 has a main body 10 and an elongated shaft 11. The shaft 11 and the main body 10 can be made of a biocompatible metallic material, for example medical grade steel.

The trocar 3 has a trocar head 15 and a cannula 16, which may be made of a biocompatible plastic such as PEEK, for example.

The medical system 1 is used in minimally invasive surgical procedures to provide an image of the surgical site. For this purpose, the trocar 3 is inserted through an incision into a body cavity (not shown) under treatment or examination, with the trocar head 15 remaining outside the patient where it can be fixed. The shaft 11 of the endoscope 2 is then inserted through the trocar 3 into the body cavity.

To enable an operative procedure in the body cavity, it is expanded with a gas, for example $CO_2$. To prevent the gas from escaping through the trocar 3, the trocar is equipped with seals 17, 18. Herein, the seal 17 is configured as a closure seal, which completely closes the trocar 3 when no instrument is inserted. The seal 18 can be a lip seal, which contacts the shaft of the instrument when it is inserted. The seals 17, 18 are made of a biocompatible elastic polymer such as silicone.

The medical system 1 further comprises an energy source in the form of a light source 20. The light source 20 is connected to the endoscope 2 via an optical fiber 21 cable. In operation, light from the light source 20 is transmitted into the endoscope via the optical fiber cable 21, where it is transmitted via optical fibers, not shown, to a distal end of the shaft 11. At the distal end of the shaft 11, the light is emitted to illuminate a field of view of the endoscope 2.

The light source 20 produces intense white light that may damage an unprotected eye. This is particularly true if the light source includes a laser light source, such as described for example in DE102016124730A1. Laser light sources are also used to generate excitation light in fluorescence examinations.

The medical system 1 further comprises a media source in the form of a pump 30 for flushing fluid. The pump 30 is connected to the endoscope 2 via a flushing tube. Flushing fluid is delivered by the pump 30 through the flushing tube into the endoscope 2, where it is delivered in the direction of an optics, not shown, to clean the optics of soiling during the procedure.

Flushing fluid from the endoscope 3 can cause fouling in an operating room, and furthermore, flushing fluid can cause a risk for accidents, such as slipping.

The medical system comprises a controller, such as the circuits described below, that prevents the delivery of energy and/or flushing fluid by the light source 20 or the pump 30 as long as the endoscope 2 is not inserted into the trocar 3.

In the embodiment shown in FIG. 1, the seals 17, 18 are made of an electrically conductive polymer. For this purpose, the polymer of the seals 17, 18 may be mixed with a metal powder or provided with a suitable coating. The seals 17, 18 are connected to a circuit 50.

When the endoscope 2 is inserted into the trocar 3, an electrical interconnection is established between the seals 17, 18 by the metallic shaft 11. This is detected by the circuit 50. The circuit 50 then generates an enabling signal, which is provided at an interface 51. The interface 51 may, for example, be a connector or a wireless interface. As a wireless interface, for example, a Bluetooth or WLAN interface may be considered. In the case of a connector, the enabling signal may be transmitted via a signal line 52.

The light source 20 and the pump 30 are configured to receive the enabling signal from the circuit 50, and to provide light or flushing fluid only when the enabling signal is present. In this way, the light source 20 or the pump 30 are safely prevented from being activated when the endoscope 2 is not inserted through the trocar 3 into the body cavity under examination or treatment. Likewise, if the endoscope 2 is retracted from the trocar 3 during the procedure, for example in order to clean it more thoroughly, this is detected by the circuit 50, and the light source 20 and/or the pump 30 can be safely deactivated before an accident risk occurs.

If the light source 20 is configured to provide both white light and laser light, white light can be provided independently of the enabling signal, while laser light is provided only when the enabling signal is present.

In the medical system 1 shown, the trocar 3 includes two electrical contacts. In principle, the insertion of the endoscope 2 into the trocar 3 may also be detected with a single contact. For this purpose, it can be determined whether an electric circuit is closed via the signal line 51 and the optical fiber cable 21 or the flushing tube 31 and the shaft 11 of the endoscope 2. For this purpose, electrical conductors may also be provided in the optical fiber cable 21 and/or the flushing tube 31.

Figure 2:
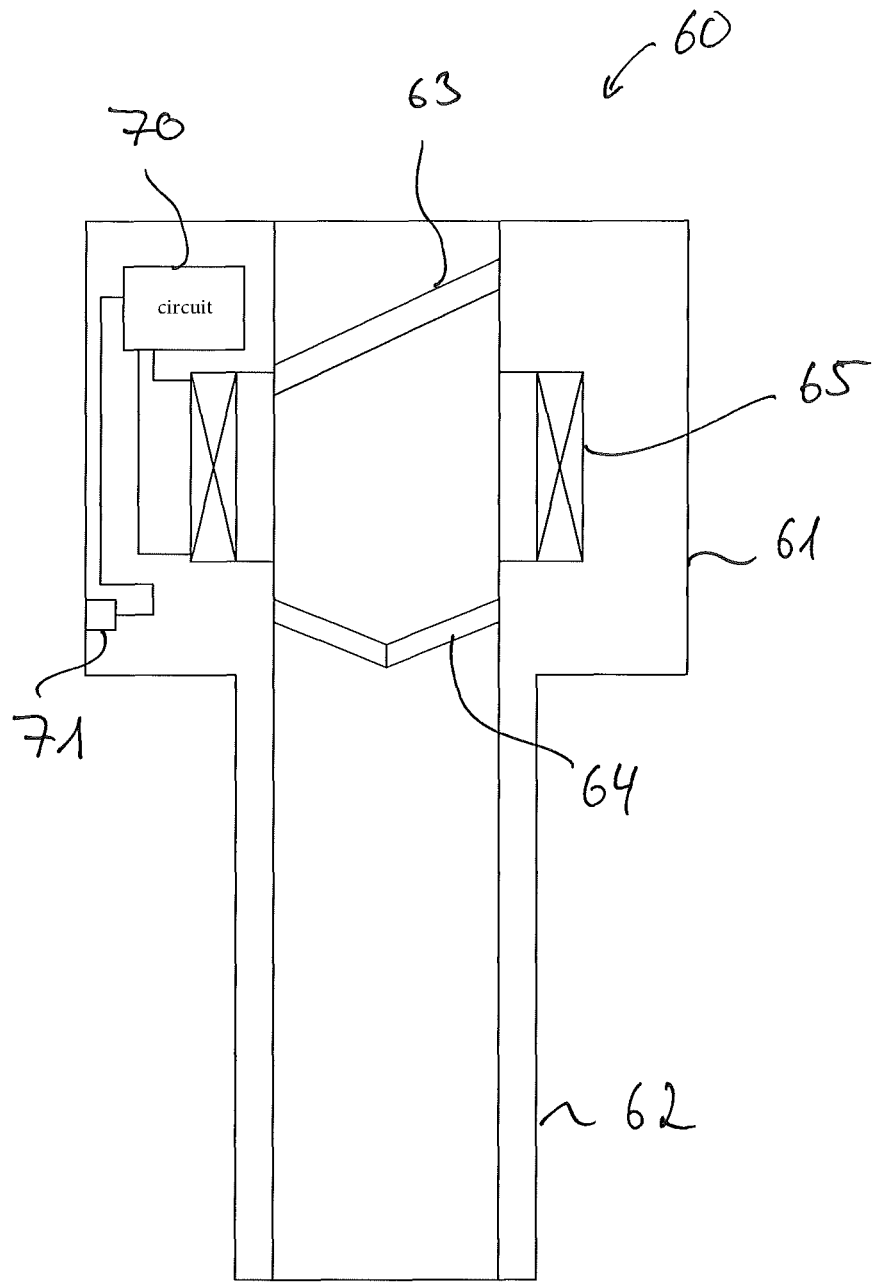
FIG. 2 illustrates a trocar.

FIG. 2 shows a trocar 60 which can be used as an alternative to the trocar 3 in the medical system 1.

The trocar 60 again comprises a trocar head 61 and a cannula 62, which is closed by seals 63, 64. In contrast to the seals 17, 18, the seals 63, 64 are not or not necessarily electrically conductive.

In the trocar head 61, a coil 65 is arranged in such a way that the endoscope 2 not shown in FIG. 2 has to be guided through the coil 65 when it is inserted into the trocar 60. In this process, the inductance of the coil 65 changes due to the magnetic, for example, ferromagnetic, behavior of the shaft 11 of the endoscope 2.

The trocar 60 further comprises a circuit 70 that measures the inductance of the coil 65. When the inductance is changed by the shaft 11, the circuit 70 generates an enabling signal and transmits it through an interface 71. The interface 71 may be similar to interface 51, for example, a connector or a wireless interface.

Figure 3:
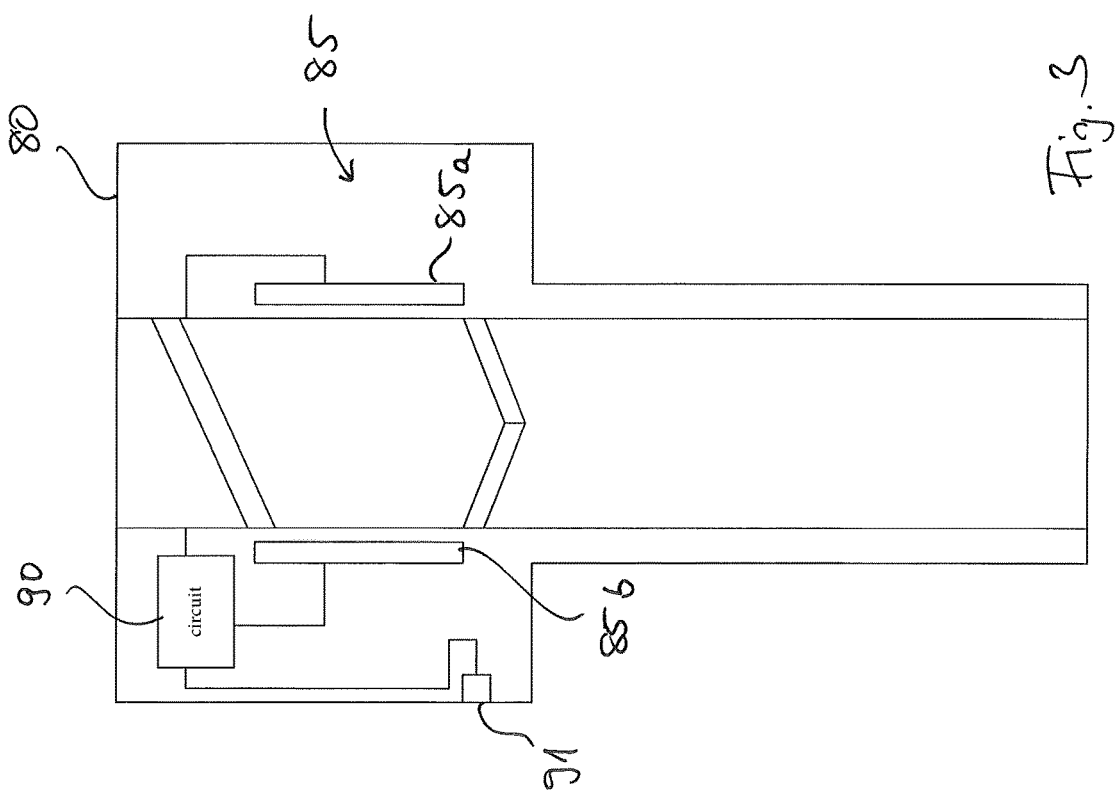
FIG. 3 illustrates another trocar.

In FIG. 3, another trocar 80 is shown which is configured similarly to trocar 60. The trocar 80 includes a capacitor 85 having two capacitor plates 85*a*, 85*b*. The capacitor 85 is arranged in such a way that an endoscope not shown in FIG. 3 reaches the vicinity of the capacitor plates 85*a*, 85*b* when inserted into the trocar 80, such as between the capacitor plates 85*a*, 85*b*. As a result, the capacitance of the capacitor 85 is changed.

The trocar 80 comprises a circuit 90 that measures the capacitance of the capacitor 85. When the capacitance is changed, the circuit 90 generates an enabling signal and transmits it through an interface 91. The interface 91 may be similar to interface 51, for example, a connector or a wireless interface.

Figure 4:
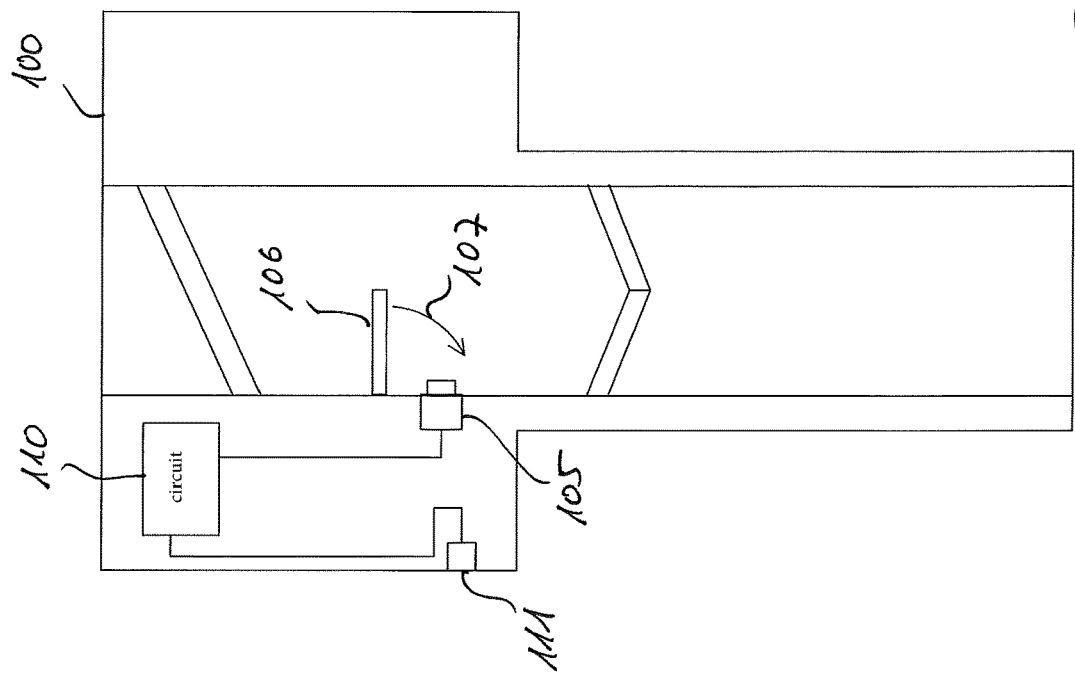
FIG. 4 illustrates still another trocar.

FIG. 4 shows yet another trocar 100, which is configured similarly to trocars 3, 60, 80 described previously. The trocar 100 comprises a tactile switch 105 which is actuated when an endoscope not shown in FIG. 4 is inserted into the trocar 100. For this purpose, a flap 106 may be arranged in the trocar 100, which is pivoted in the direction of the arrow 107 by the endoscope and actuates the tactile switch 105. The flap 106 may be biased against the direction of arrow 107 by a spring not shown, so that it moves back to the position shown in FIG. 4 after the endoscope is retracted from the trocar 100.

The trocar 100 includes a circuit 110 that evaluates the switch position of the tactile switch 105. When the tactile switch 105 is actuated, the circuit 110 generates an enabling signal and transmits it through an interface 111. The interface 111 may be similar to interfaces 51, 71, for example, a connector or a wireless interface.

The trocars 3, 60, 80, 100 may be configured to be reusable. For this purpose, the circuits 50, 70, 90, 110 must be sufficiently protected from damage during a reprocessing procedure. Alternatively, the trocars 3, 60, 80, 100 may be configured for single use. In this case, the circuits 50, 70 may be relatively inexpensive when provided as printed circuits, and need not be protected from the effects of a reprocessing process.

A simple battery can be provided as the power supply for the circuits 50, 70, 90, 110, for example a button cell. Alternatively, an external power supply not shown is also possible.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A medical system comprising:
   a trocar configured to provide an artificial access to a body cavity of a patient, the trocar having an interior channel and a seal disposed in the interior channel;
   a medical instrument having a shaft configured to be inserted through the interior channel of the trocar and into the body cavity of the patient for performing a medical function in the body cavity of the patient, the shaft comprising a conductive outer circumferential surface, the seal configured to seal against the outer circumferential surface of the shaft when the shaft is inserted through the interior channel;
   the seal being conductive and configured to come into contact with the conductive outer circumferential surface of the shaft when the shaft is inserted into the trocar to close a circuit; and
   a controller configured to:
   determine whether the medical instrument is inserted into the trocar based on closing of the circuit; and
   enable the performing of the medical function by the medical instrument only if the medical instrument is determined to be inserted into the trocar.

2. The medical system according to claim 1, further comprising one or more of a media source and an energy source configured to provide media and energy, respectively, for the performing of the medical function;
   wherein the controller is configured to enable one or more of the media source and the energy source only when the medical instrument is determined to be inserted into the trocar.

3. The medical system according to claim 2, wherein the medical instrument is an endoscope.

4. The medical system according to claim 3, wherein the media source is configured to provide flushing fluid.

5. The medical system according to claim 3, wherein the energy source comprises a light source.

6. The medical system according to claim 5, wherein the light source comprises a laser light source.

7. The medical system according to claim 1, wherein the seal comprises an electrically conductive elastic polymer.

8. The medical system according to claim 1, wherein the circuit is integrated in the trocar.

9. The medical system according to claim 1, wherein the controller is configured to provide one of a wireless or wired enabling signal when the medical instrument is determined to be inserted into the trocar.

10. A trocar comprising:
    an internal channel configured to accept a shaft of a medical instrument;
    a seal disposed in the interior channel, the seal configured to seal against an outer circumferential surface of the shaft when the shaft is inserted through the interior channel, the seal being conductive and configured to come into contact with the conductive outer circumferential surface of the shaft when the shaft is inserted into the trocar to close a circuit; and
    a controller configured to:

determine whether the medical instrument is inserted into the trocar based on closing of the circuit; and enable performing of a medical function by the medical instrument only if the medical instrument is determined to be inserted into the trocar.

11. The trocar according to claim 10, wherein the seal comprises an electrically conductive elastic polymer.

12. The trocar according to claim 10, wherein the circuit is integrated in the trocar.

13. The trocar according to claim 10, wherein the controller is configured to provide one of a wireless or wired enabling signal when the medical instrument is determined to be inserted into the trocar.

* * * * *